(12) United States Patent
Scooros

(10) Patent No.: US 12,150,676 B2
(45) Date of Patent: Nov. 26, 2024

(54) SKIN TREATMENT APPARATUS WITH COOLING MEMBER

(71) Applicant: FKA Distributing Co., LLC, Commerce Township, MI (US)

(72) Inventor: Lori Scooros, Macomb, MI (US)

(73) Assignee: FKA Distributing Co., LLC, Commerce Township, MI (US)

( * ) Notice: Subject to any disclaimer, the term of this patent is extended or adjusted under 35 U.S.C. 154(b) by 99 days.

(21) Appl. No.: 17/968,878

(22) Filed: Oct. 19, 2022

(65) Prior Publication Data

US 2023/0045459 A1 Feb. 9, 2023

Related U.S. Application Data

(62) Division of application No. 16/816,879, filed on Mar. 12, 2020, now Pat. No. 11,504,159.

(Continued)

(51) Int. Cl.
*A61B 17/54* (2006.01)
*A61F 7/00* (2006.01)
(Continued)

(52) U.S. Cl.
CPC ............... *A61B 17/54* (2013.01); *A61F 7/00* (2013.01); *A61B 2017/00398* (2013.01); *A61B 2017/00734* (2013.01); *A61B 2017/00761* (2013.01); *A61B 2017/320074* (2017.08); *A61B 2090/0807* (2016.02); *A61B 2217/005* (2013.01);
(Continued)

(58) Field of Classification Search
CPC .................. A61B 17/54; A61B 17/545; A61B 2017/00398; A61B 2017/00734; A61B 2017/00761; A61B 2018/0047; A61B 2018/00708; A61B 2090/0807; A61B 2217/00; A61B 17/320068; A61B 2017/00473; A61B 2017/00747; A45D 2200/207; A45D 27/00; A45D 26/0057; A45D 29/14

See application file for complete search history.

(56) References Cited

U.S. PATENT DOCUMENTS 10,172,644 B2 1/2019 Ignon et al.
2006/0058714 A1 3/2006 Rhoades
(Continued)

FOREIGN PATENT DOCUMENTS

KR 20050012037 A 1/2005
WO 2011001345 A1 1/2011
(Continued)

OTHER PUBLICATIONS

English machine translation for WO 2015/052929 A1, 2015, 15 pages.
(Continued)

*Primary Examiner* — Katherine M Shi
(74) *Attorney, Agent, or Firm* — Brooks Kushman P.C.

(57) ABSTRACT

A skin treatment apparatus, such as a microdermabrasion or dermaplaning apparatus, includes a housing having a top end and a bottom end, a treatment head attached to the top end of the housing and arranged to exfoliate skin within a treatment area, and a cooling member provided on the bottom end of the housing arranged to cool skin within the treatment area.

9 Claims, 12 Drawing Sheets

Related U.S. Application Data

(60) Provisional application No. 62/817,900, filed on Mar. 13, 2019.

(51) Int. Cl.
  *A61B 17/00* (2006.01)
  *A61B 17/32* (2006.01)
  *A61B 90/00* (2016.01)

(52) U.S. Cl.
  CPC ............... *A61F 2007/0052* (2013.01); *A61F 2007/0075* (2013.01)

(56) References Cited

U.S. PATENT DOCUMENTS

| | | | |
|---|---|---|---|
| 2007/0178121 A1* | 8/2007 | First | A61K 8/64 424/70.13 |
| 2010/0049177 A1 | 2/2010 | Boone, III et al. | |
| 2011/0009809 A1 | 1/2011 | Bielfeldt et al. | |
| 2011/0040235 A1 | 2/2011 | Castel | |
| 2011/0106067 A1 | 5/2011 | Geva et al. | |
| 2012/0090181 A1 | 4/2012 | Broekhuizen et al. | |
| 2013/0158547 A1 | 6/2013 | David | |
| 2014/0336540 A1 | 11/2014 | Chen | |
| 2015/0073438 A1* | 3/2015 | Levy | A45D 44/22 606/131 |
| 2015/0209108 A1 | 7/2015 | Kim | |
| 2017/0079676 A1* | 3/2017 | Ceto | A61B 17/54 |
| 2018/0353101 A1 | 12/2018 | Ouwerkerk et al. | |
| 2019/0038353 A1 | 2/2019 | Fatemi | |
| 2019/0365461 A1* | 12/2019 | Saeki | A61B 18/1206 |

FOREIGN PATENT DOCUMENTS

| | | |
|---|---|---|
| WO | 2011051941 A1 | 5/2011 |
| WO | 2015034530 A1 | 3/2015 |
| WO | 2015052929 A1 | 4/2015 |

OTHER PUBLICATIONS

International Search Report and Written Opinion for Application No. PCT/US2020/022357, dated Jul. 2, 2020, 14 pages.
Homedics, "Duo Climate™ Hot and Cold Sonic Facial Wand", FAC-420, Instruction Manual, Oct. 30, 2017, 30 pages.
Homedics, "Radiance Microdermabrasion", MDA-100, Instruction Manual, Dec. 7, 2017, 19 pages.
Extended European Search Report for Application No. 20770624.3, dated Nov. 8, 2022, 7 pages.
Europe Examination Report for Application No. 20770624.3, dated Apr. 24, 2024, 5 pages.

\* cited by examiner

SKIN TREATMENT APPARATUS WITH COOLING MEMBER

CROSS-REFERENCE TO RELATED APPLICATIONS

This application is a division of U.S. application Ser. No. 16/816,879 filed Mar. 12, 2020, which claims the benefit of U.S. provisional application Ser. No. 62/817,900 filed Mar. 13, 2019, the disclosures of which are hereby incorporated in their entirety by reference herein.

TECHNICAL FIELD

Embodiments relate to a skin treatment apparatus having a cooling member for contacting and cooling a user's skin.

BACKGROUND

Beauty treatments such as microdermabrasion or dermaplaning can help restore and maintain a youthful appearance of the skin. In both the clinical and home environments, cooling of the skin following treatment involving any type of dermal abrasion or exfoliation can provide many benefits. Direct skin cooling may minimize epidermal damage, and cooling of the upper dermis is protective and may relieve any post-treatment pain. Decreasing the temperature of the skin through cooling may also affect how the skin interacts with beauty products, such as skin cream or make-up.

SUMMARY

In one or more embodiments, a skin treatment apparatus includes a housing having a top end and a bottom end, a treatment head attached to the top end of the housing and arranged to exfoliate skin within a treatment area, and a cooling member provided on the bottom end of the housing arranged to cool skin within the treatment area.

In one or more embodiments, a microdermabrasion apparatus includes a housing having a top end and a bottom end. A microdermabrasion treatment head is attached to the top end of the housing and has a top rim arranged to exfoliate skin within a treatment area. A cooling member is provided on the bottom end of the housing arranged to cool skin within the treatment area.

In one or more embodiments, a dermaplaning apparatus includes a housing having a top end and a bottom end, a trimming head attached to the top end housing and having a blade assembly arranged to exfoliate skin within a treatment area, and a cooling member provided on the bottom end of the housing and arranged to cool skin within the treatment area.

DETAILED DESCRIPTION

Figure 1:
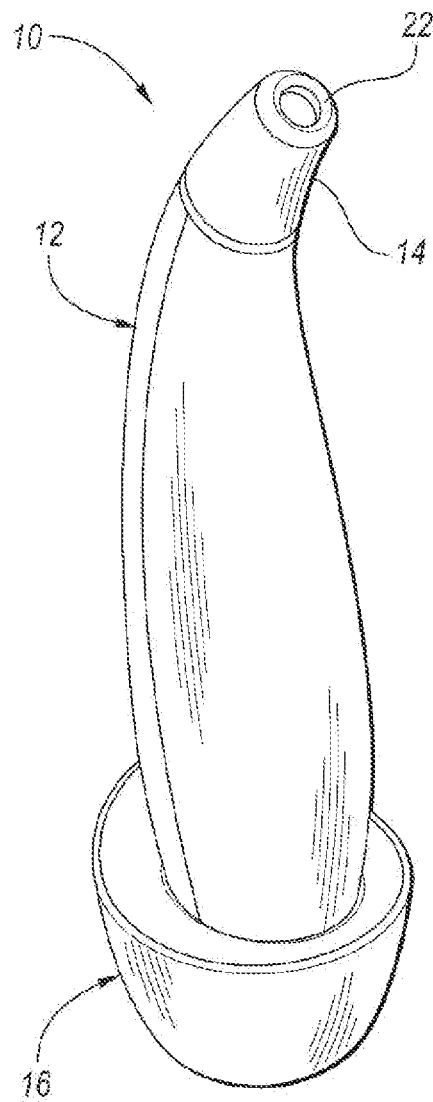
FIG. 1 is a front perspective view of a microdermabrasion apparatus received in a charging base according to an embodiment.
Figure 2:
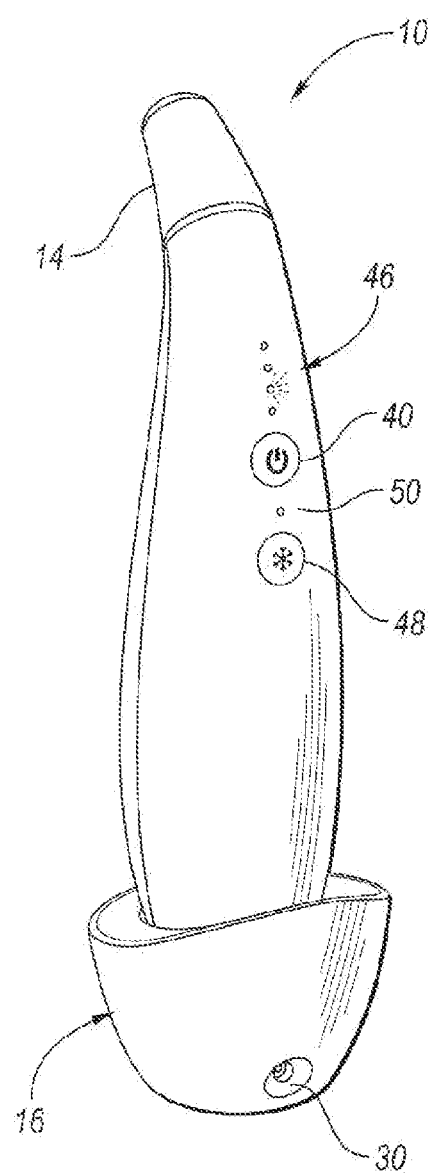
FIG. 2 is a rear perspective view of the microdermabrasion apparatus and charging base of FIG. 1.
Figure 5:
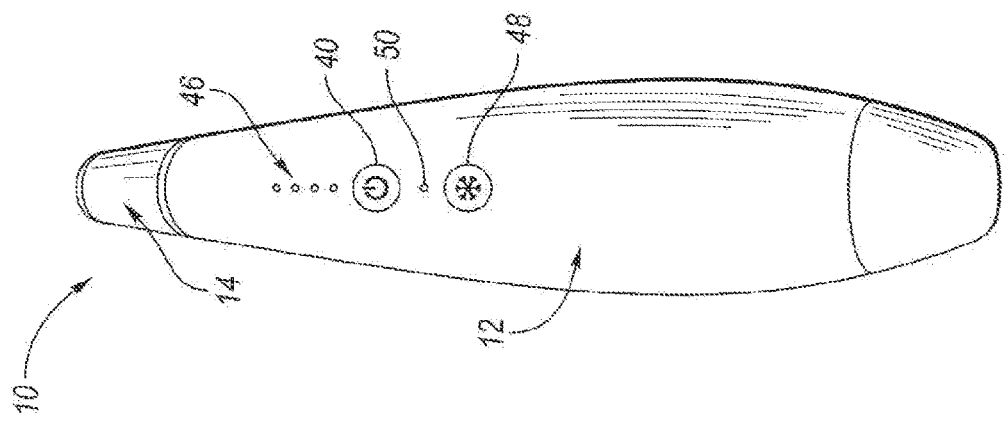
FIG. 5 is a rear view of the microdermabrasion apparatus of FIG. 1.
Figure 4:
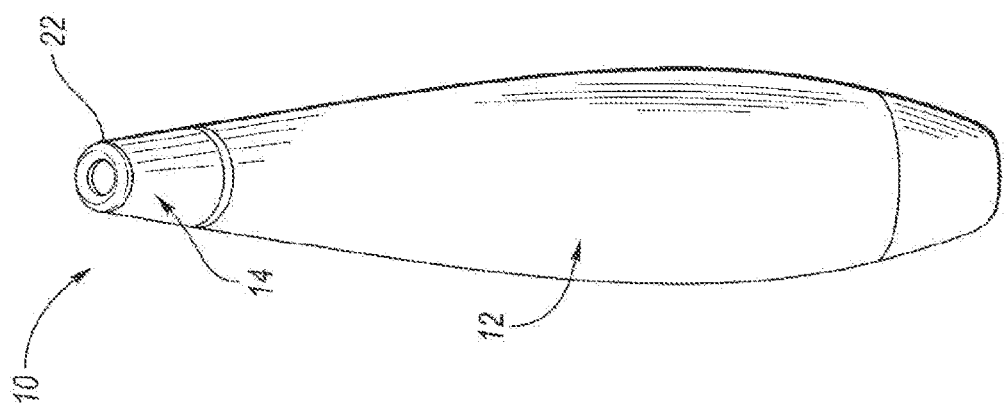
FIG. 4 is a front view of the microdermabrasion apparatus of FIG. 1.
Figure 3:
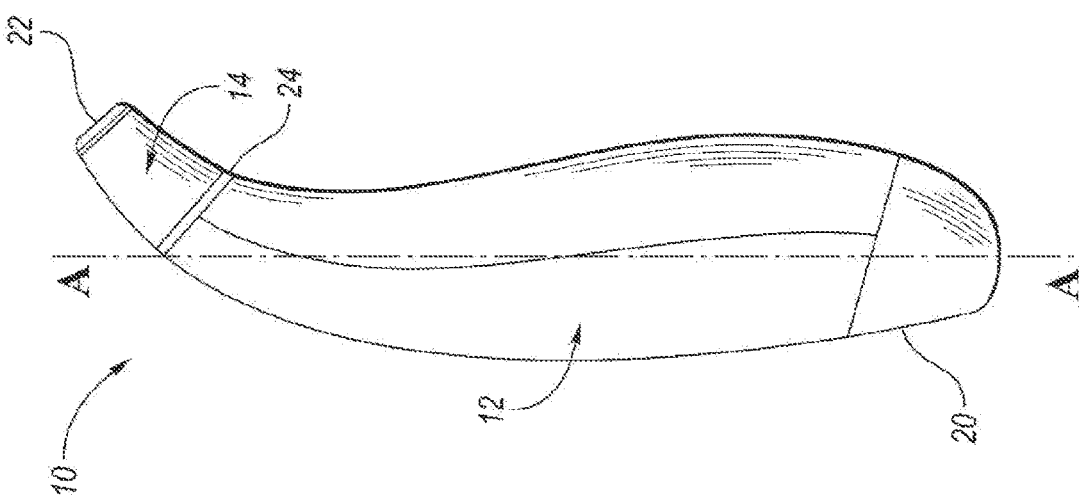
FIG. 3 is a side view of the microdermabrasion apparatus of FIG. 1.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Embodiments disclosed herein include skin treatment apparatuses which include a cooling member, such as for providing cooling of the skin following dermal treatments, such as abrasion or exfoliation. For example, cooling of the skin may be beneficial in tightening and sealing the skin while reducing any redness and puffiness. The embodiments described herein conveniently and advantageously provide a cooling function for the skin within the same apparatus as the dermal treatment function.

With reference first to FIGS. 1-6, a microdermabrasion apparatus 10 is illustrated. The microdermabrasion apparatus 10 includes a housing 12 and a microdermabrasion treatment head 14 attached to the housing 12, where the microdermabrasion apparatus 10 can be received in a charging base 16 as shown. In one or more embodiments, the housing 12 may be elongated and generally curved to facilitate gripping by a user and ergonomic access to the user interface, described further below. The charging base 16 may be generally cylindrical and formed with a recess 18 (FIG. 6) for receiving at least a bottom end 20 of the housing 12 of the microdermabrasion apparatus 10. Although a particular shape of the housing 12 and charging base 16 are illustrated, it is understood that the microdermabrasion apparatus 10 is not limited to these shapes.

The microdermabrasion treatment head 14 may be generally cylindrical with a hollow interior. The microdermabrasion treatment head 14 has a top rim 22 which may comprise a microcrystalline or diamond material, wherein the top rim 22 may be placed against a user's skin and moved across the surface of the skin to provide exfoliation while suction (described below with reference to FIG. 16) is applied. As shown, the microdermabrasion treatment head 14 may be received on the housing 12 so as to extend forward of or offset from a longitudinal central axis A-A of the housing 12, wherein this position may facilitate and optimize contact of the microdermabrasion treatment head 14 with a user's face. The microdermabrasion treatment head 14 may be integral with the housing 12, or may be removably secured to a top end 24 of the housing 12 via a snap fit, slidable or threaded connection, for example.

The microdermabrasion treatment head 14 and suction act to exfoliate the skin, removing dead cells from the skin surface, revealing and stimulating the fresh skin layer beneath. The microdermabrasion apparatus 10 can function to restore youthful radiance to the skin, improve skin tone and texture, smooth the appearance of fine lines and wrinkles and reduce the appearance of age spots and sun damage. Multiple removable and interchangeable microdermabrasion treatment heads 14 with top rims 22 having different surface characteristics, and therefore different sensitivities, may be included for use with the microdermabrasion apparatus 10.

Figure 6:
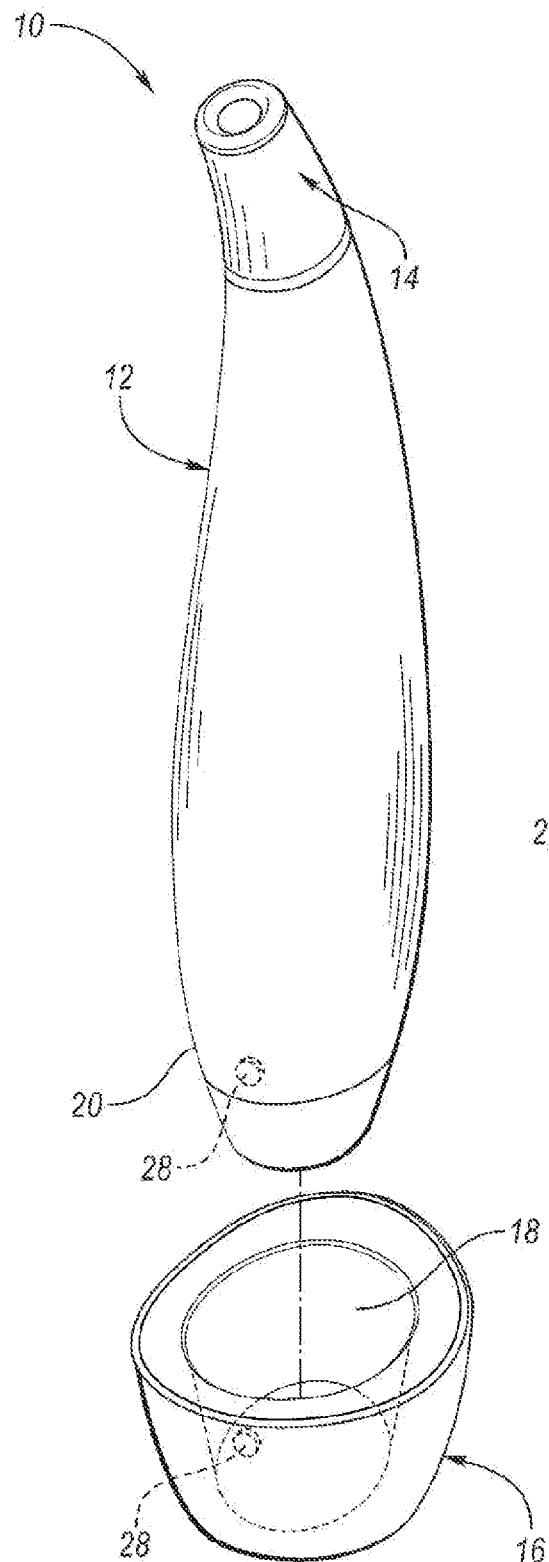
FIG. 6 is a front perspective view of the microdermabrasion apparatus of FIG. 1 shown removed from the charging base.
Figure 7:
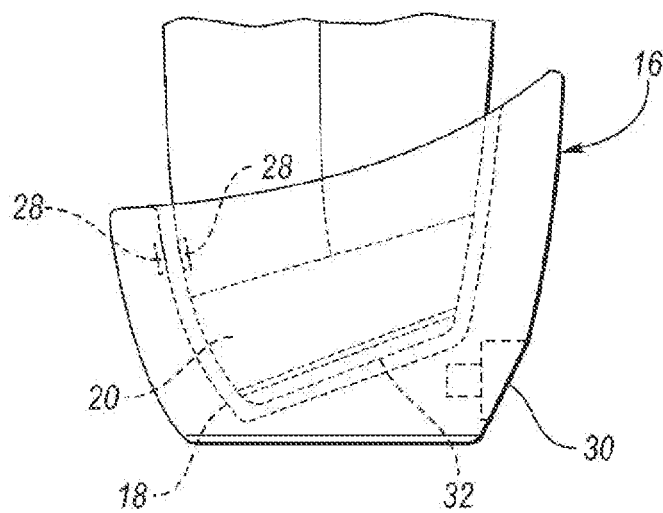
FIG. 7 is a cross-sectional view of a bottom end of the microdermabrasion apparatus received in the charging base, wherein the induction charging points are illustrated.
Figure 15:
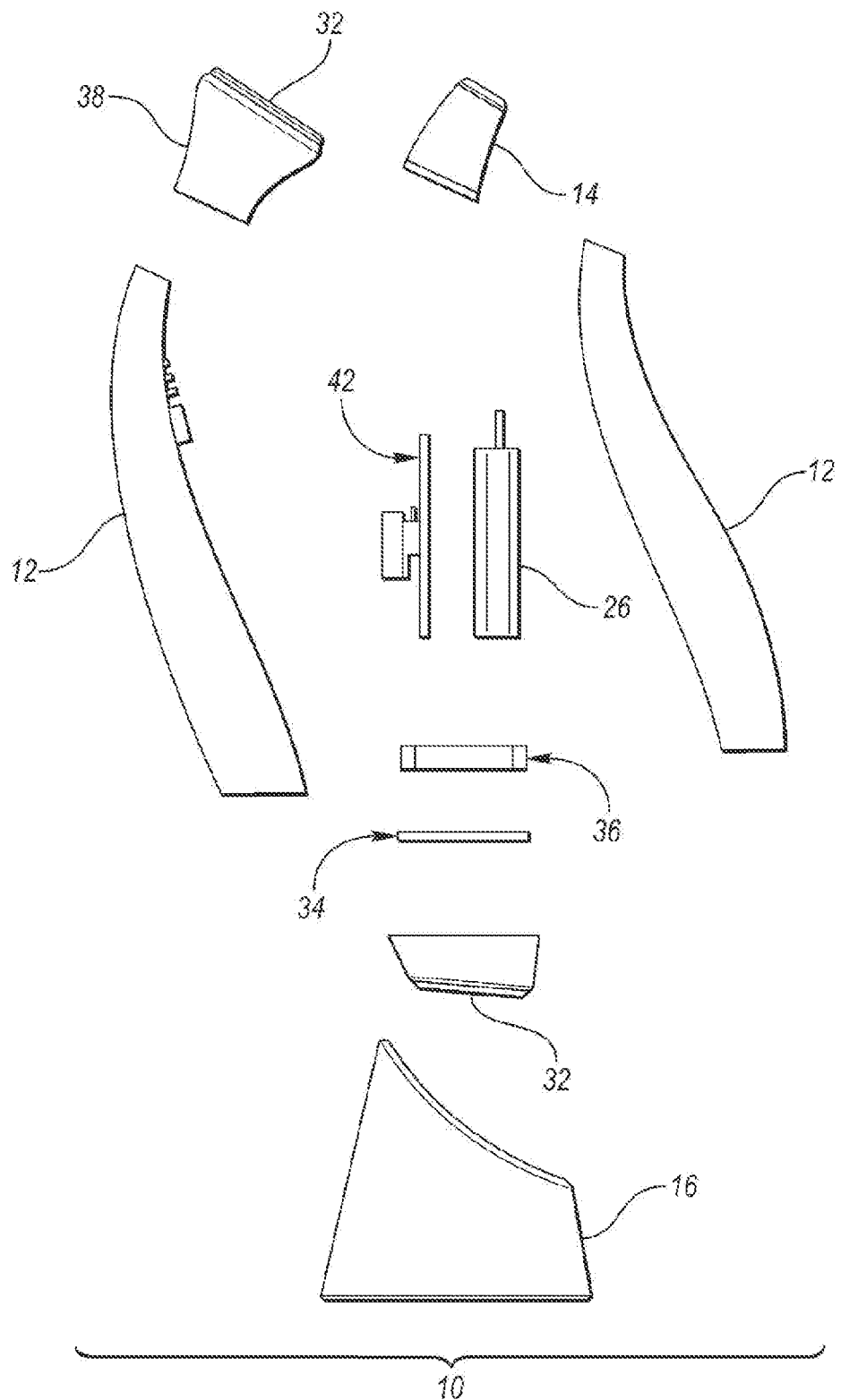
FIG. 15 is an exploded view of the microdermabrasion apparatus illustrating both the microdermabrasion treatment head and the cooling treatment head along with the cooling plate and the charging base.
Figure 16:
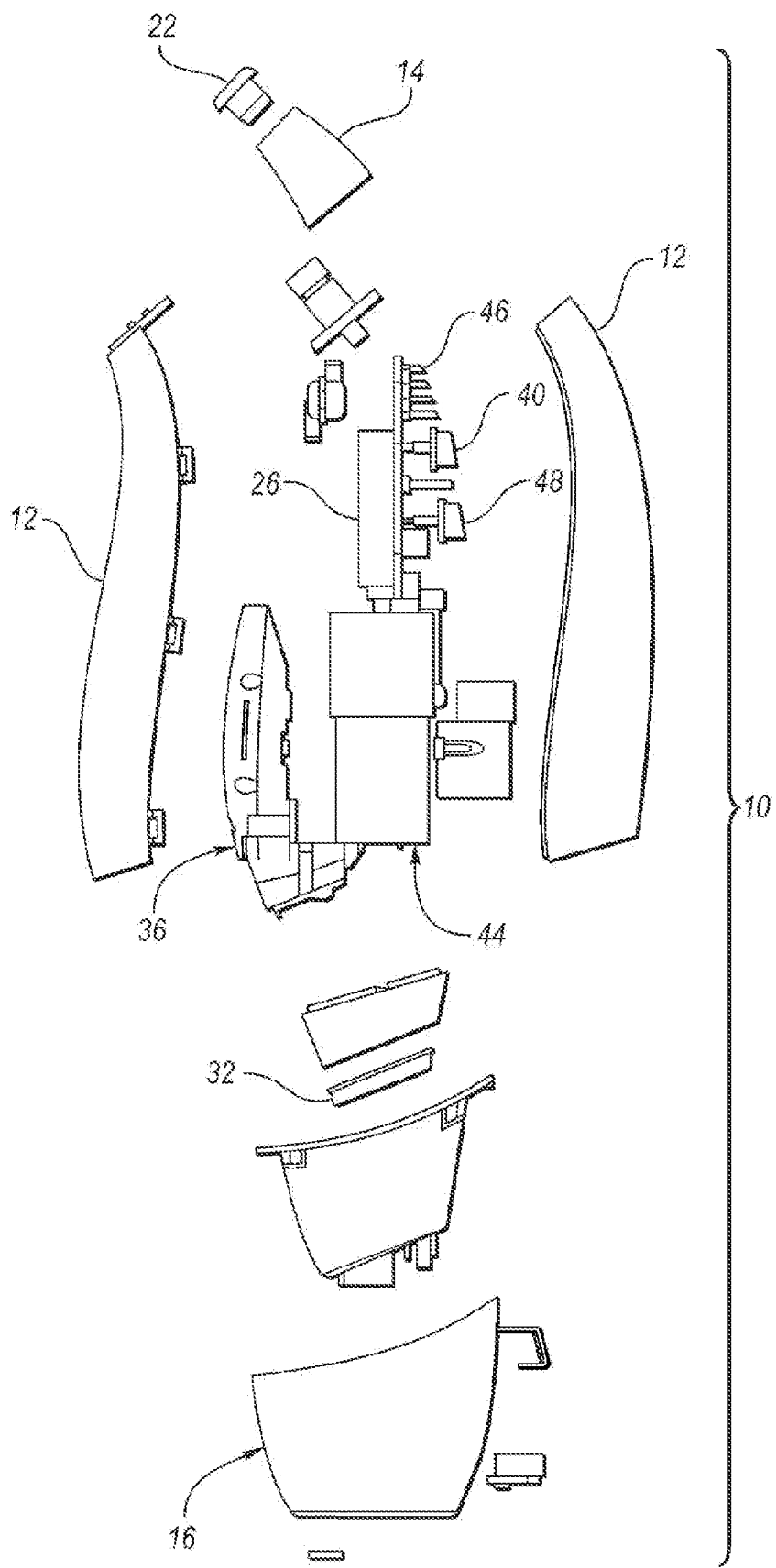
FIG. 16 is an exploded view of the microdermabrasion apparatus illustrating internal mechanical and electrical components.
Figure 17:
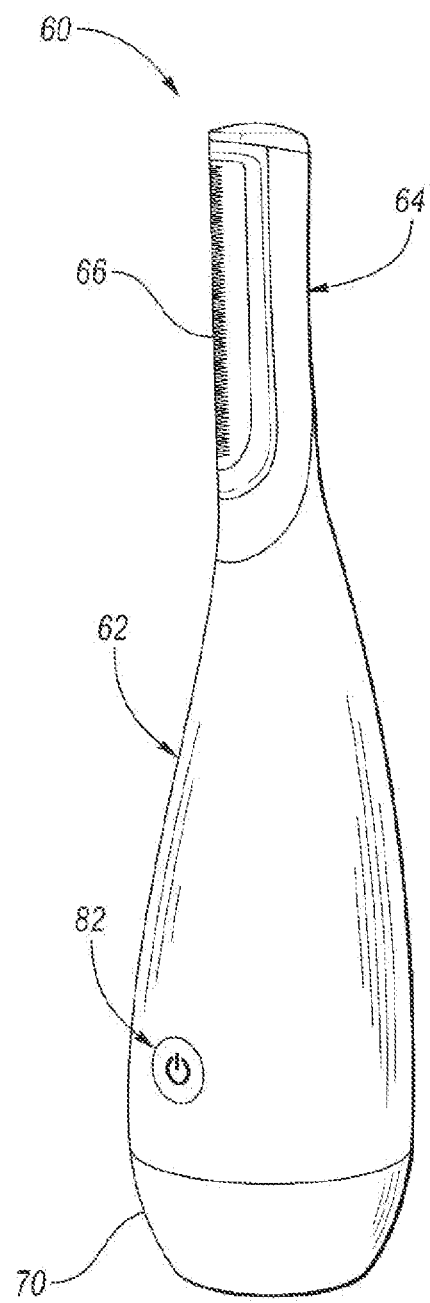
FIG. 17 is a front perspective view of a dermaplaning apparatus according to an embodiment.

In one or more embodiments, the microdermabrasion apparatus 10 is rechargeable and includes an internal rechargeable (e.g. lithium) battery 26 (FIGS. 15 and 16). FIGS. 6 and 7 illustrate induction charging points 28 on the housing 12 and the interior of the charging base 16 as well as a charging port 30 on the exterior of the charging base 16. To charge the microdermabrasion apparatus 10 via induction charging, the bottom end 20 of the housing 12 may be inserted into the recess 18 of the charging base 16, and the charging base 16 is connected to an electrical outlet or other power source by a charging cord (not shown) received in the charging port 30. Alternatively, the charging port 30 may be provided on the housing 12 for directly charging the microdermabrasion apparatus 10, such that the charging base 16 would not be required.

Figure 8:
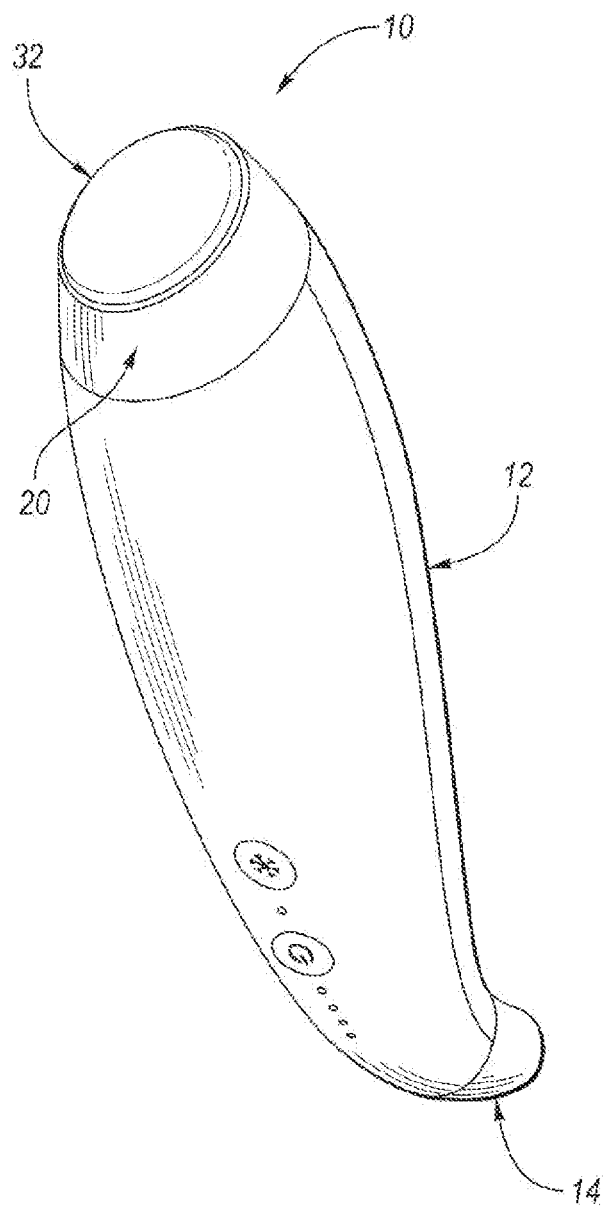
FIG. 8 is an inverted front perspective view of the microdermabrasion apparatus of FIG. 1 illustrating a cooling plate on the bottom end of the microdermabrasion apparatus.
Figure 11:
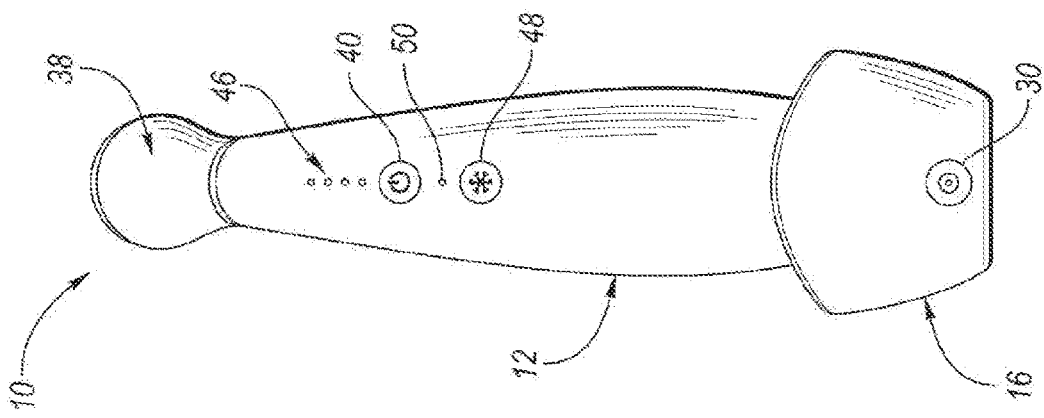
FIG. 11 is a rear view of the microdermabrasion apparatus of FIG. 9 received in the charging base.
Figure 10:
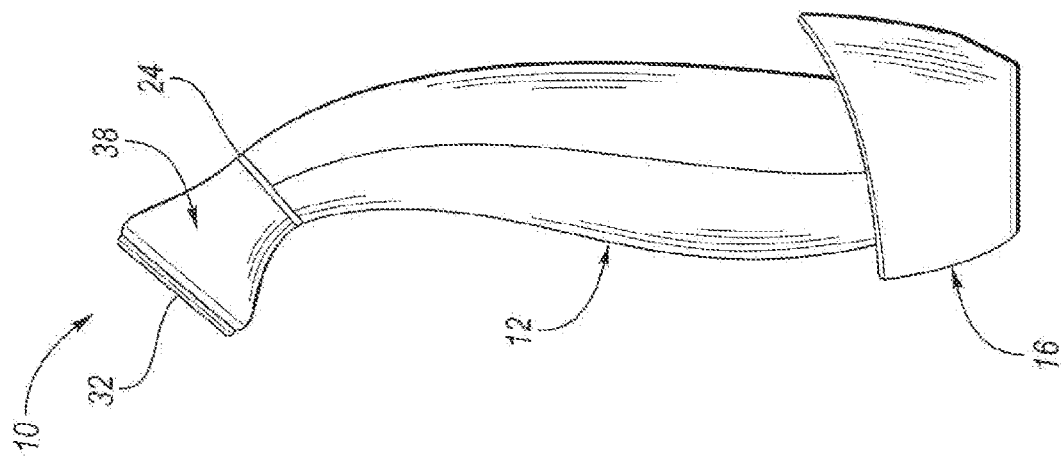
FIG. 10 is a side view of the microdermabrasion apparatus of FIG. 9 received in the charging base.
Figure 9:
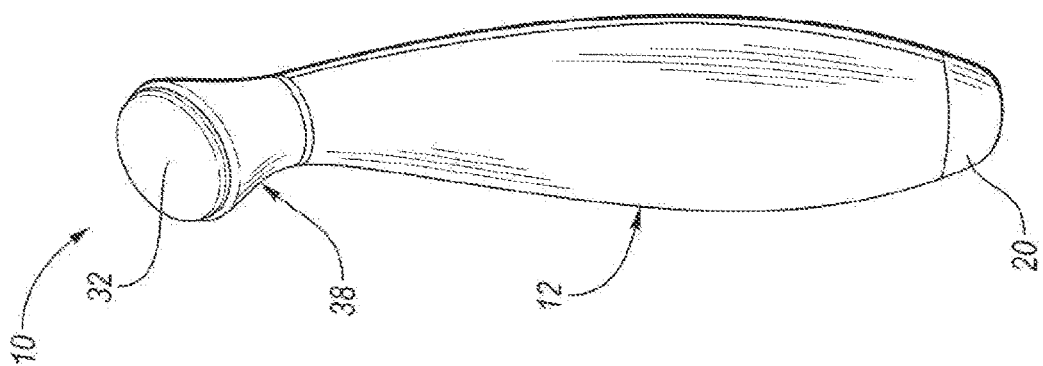
FIG. 9 is a front perspective view of another embodiment of the microdermabrasion apparatus where a microdermabrasion treatment head is replaced with a cooling treatment head.
Figure 14:
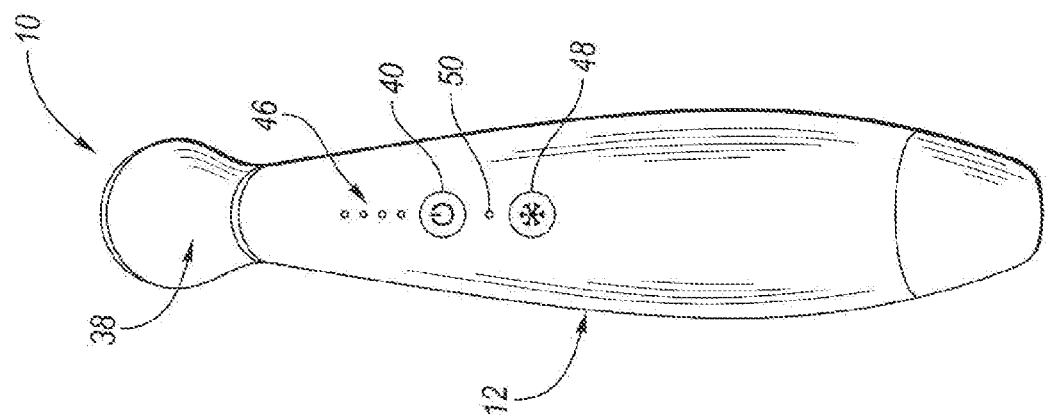
FIG. 14 is a rear view of the microdermabrasion apparatus of FIG. 9.
Figure 13:
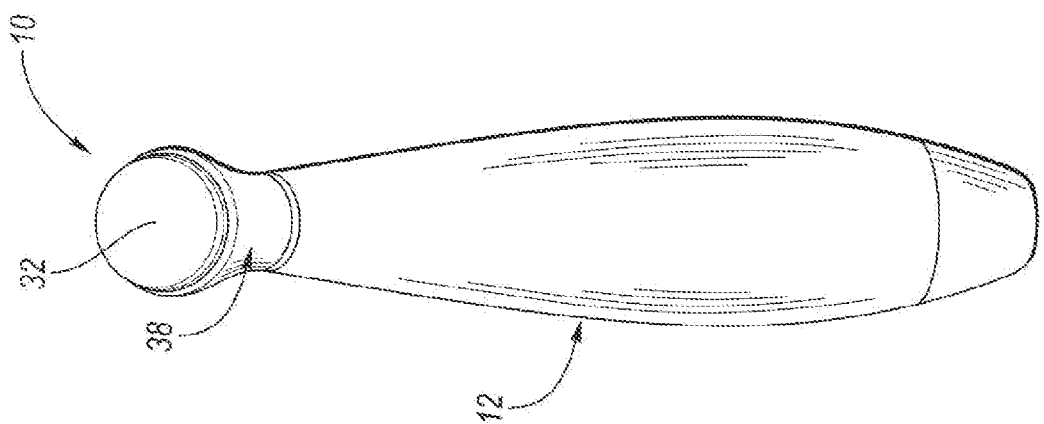
FIG. 13 is a front view of the microdermabrasion apparatus of FIG. 9.
Figure 12:
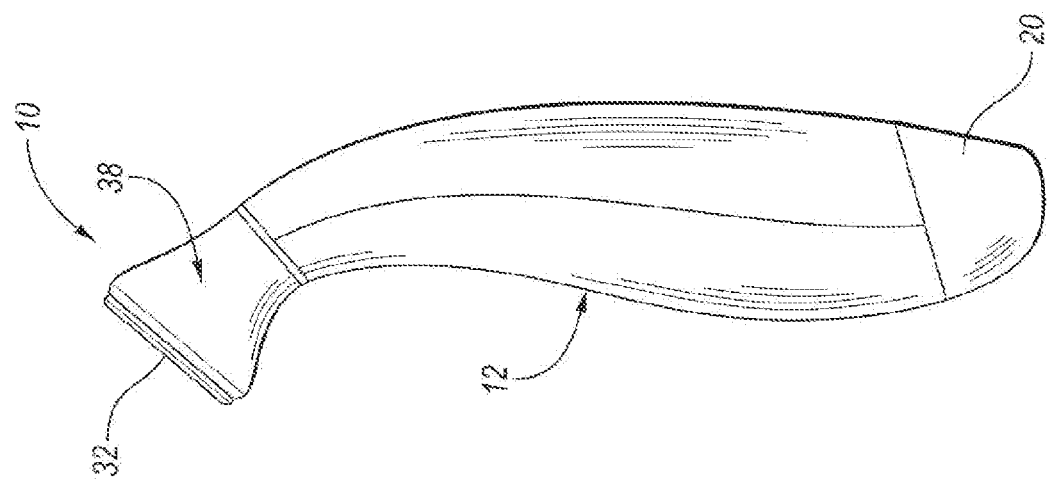
FIG. 12 is a side view of the microdermabrasion apparatus of FIG. 9.

FIG. 8 is an inverted front perspective view of the microdermabrasion apparatus 10 illustrating a cooling member 32 such as a cooling plate provided on the bottom end 20 of the housing 12 of the microdermabrasion apparatus 10. The cooling member 32 may be used to contact and cool skin within a treatment area after exfoliation by the microdermabrasion treatment tip 14, or may be generally used for cooling the skin at other times or in other regions. In one or more embodiments, the cooling member 32 may be constructed from a metallic material and may be cooled by a thermoelectric cooler or Peltier device or Peltier chip 34, as illustrated in FIG. 15. In a non-limiting example, the cooling member 32 may be capable of reaching a temperature less than 9 degrees C. in less than 60 seconds and between approximately 0-9 degrees C. in an elapsed time of 60-150 sec. The cooling member 32 can be generally planar and circular- or oval-shaped as shown or could alternatively have other shapes and/or textures.

As is known in the art, thermoelectric coolers may operate by the Peltier effect, which creates a temperature difference by transferring heat between two electrical junctions. A Peltier device has two sides, and a voltage is applied across joined conductors to create an electric current. When a DC electric current flows through the Peltier device it transfers heat from one side to the other so that one side gets cooler while the other gets hotter. The "hot" side is attached to a heat sink 36 (FIGS. 15 and 16) so that it remains at ambient temperature, while the "cool" side is below room temperature. In operation, the cool side absorbs heat which is then transferred to the hot side of the Peltier device. In some instances, multiple thermoelectric coolers may be connected and placed between two metal or ceramic plates.

As an alternative or in addition to the integral cooling member 32 or cooling plate described above, a removable cooling treatment head 38 having a cooling member 32 may be provided. FIGS. 9-14 illustrate another embodiment of the microdermabrasion apparatus 10 which includes a removable cooling treatment head 38 which is interchangeable with the microdermabrasion treatment head 14. In this embodiment, after exfoliation of skin within a treatment area using the microdermabrasion treatment head 14, the head 14 can be interchanged with the cooling treatment head 38 which can then be applied to cool skin within a treatment area. Alternatively, the cooling treatment head 38 may be generally used for contacting and cooling the skin at other times or in other regions. As above, the cooling member 32 on the removable cooling treatment head 38 may be constructed from a metallic material and may be cooled by a Peltier chip 34, wherein the Peltier chip 34 may be disposed within the housing 12 or within the cooling treatment head 38 itself. Also, as above, the cooling member 32 on the cooling treatment head 38 can be generally planar and circular- or oval-shaped as shown or could alternatively have other shapes and/or textures.

The microdermabrasion apparatus 10 includes a power button 40 which can function to turn the microdermabrasion apparatus 10 on and off as well as to toggle through different treatment levels. A controller or printed circuit board (PCB) 42 in electrical communication with a vacuum pump 44 (FIGS. 15 and 16) can provide multiple suction intensity levels through the microdermabrasion treatment head 14 to provide optimal comfort and effectiveness to a user. Different suction levels may be used for different areas of the face, for example, where a lower suction level may be recommended around the sensitive eye area while a higher suction level may be possible around the forehead and nose areas. In one non-limiting example, different suction levels of the vacuum pump 44 may include: Level 1: 1.0-1.9 L/min; Level 2: 1.6-2.3 L/min; Level 3: 2.0-2.8 L/min; Level 4: 2.6-3.4 L/min.

Indicator lights 46, such as LEDs, may be provided to indicate when the microdermabrasion apparatus 10 is powered on and to indicate the selected treatment level. The indicator lights 46 may also be used to indicate charging progress of the battery 26. The microdermabrasion apparatus 10 can also include a cooling power button 48 for powering the cooling member 32, either integrally formed on the bottom end 20 of the housing 12 of the microdermabrasion apparatus 10 or removable attached via the cooling head 38, on and off as well as a corresponding cooling mode indicator light 50.

Figures 19, 20:
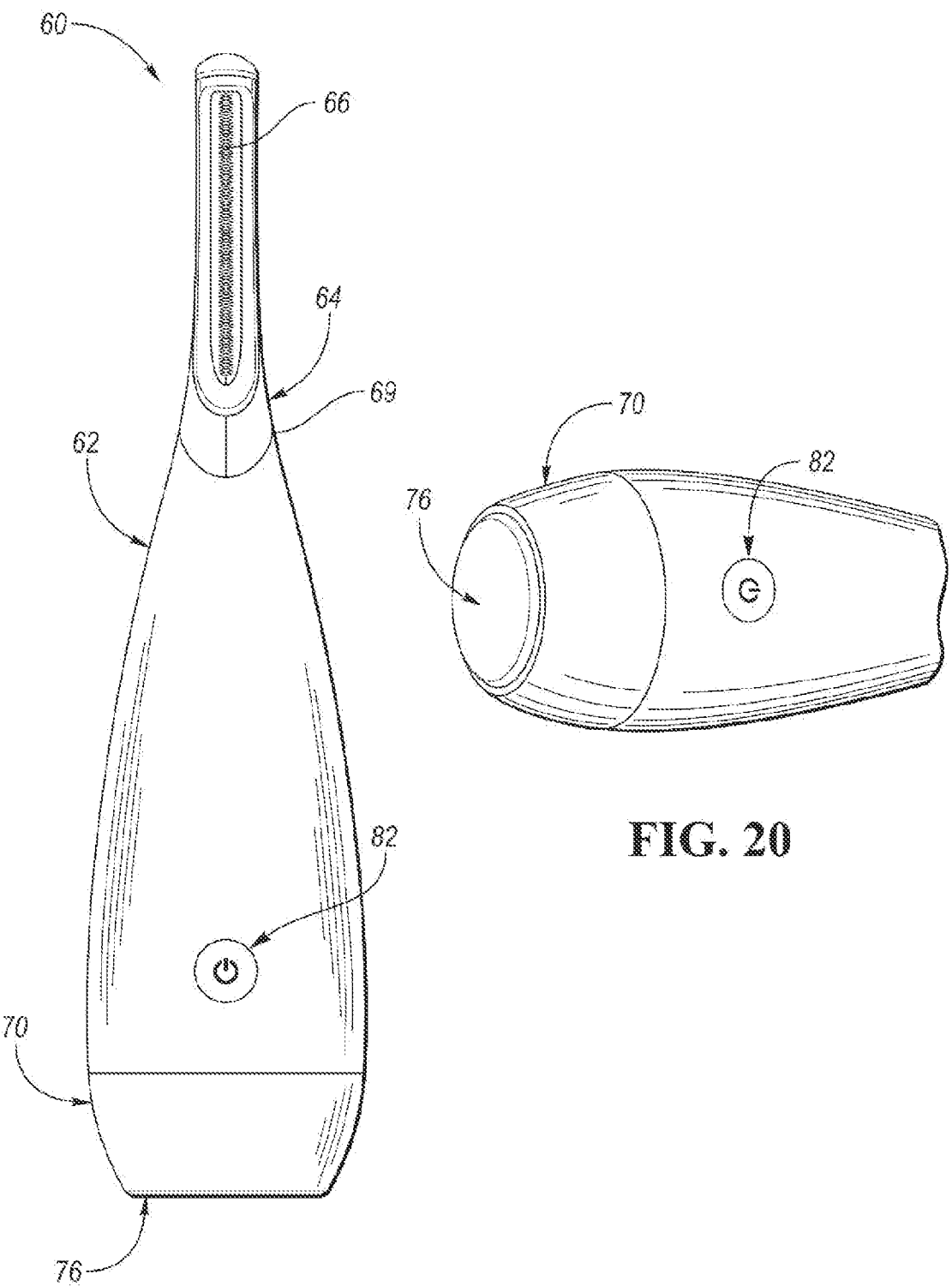
FIG. 19 is a front view of the dermaplaning apparatus.
FIG. 20 is a side perspective view of a bottom end of the dermaplaning apparatus illustrating a cooling plate.
Figure 21:
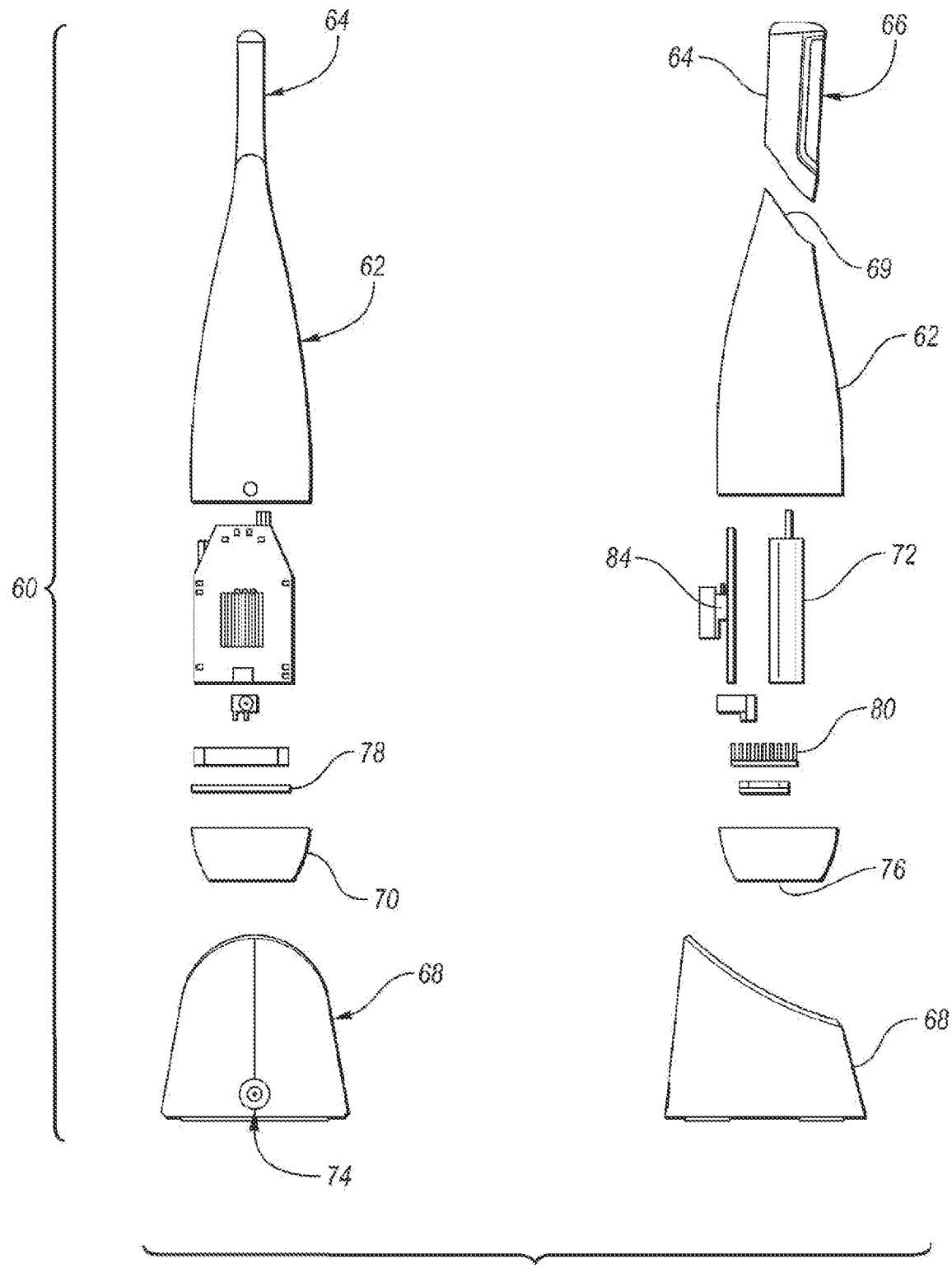
FIG. 21 is an exploded view of the dermaplaning apparatus illustrating the cooling plate and the charging base.

Turning now to FIGS. 17-22, a dermaplaning apparatus 60 is illustrated. The dermaplaning apparatus 60 includes a housing 62 and a trimming head 64 which includes a blade or blade assembly 66, where the dermaplaning apparatus 60 can be received in a charging base 68 (FIG. 21). In one or more embodiments, the housing 62 may be elongated in shape, such as to facilitate gripping by a user. The trimming head 64 may be integral with the housing 62 or may be removably secured to a top end 69 of the housing 62 via a snap fit, slidable, or threaded connection, for example. The blade assembly 66 may likewise be removable from the trimming head 64. The charging base 68 may be generally cylindrical and formed with a recess (such as recess 18 illustrated in FIG. 6 for charging base 16) for receiving at least a bottom end 70 of the housing 62 of the dermaplaning apparatus 60. Although a particular shape of housing 62 and charging base 68 are illustrated, it is understood that the dermaplaning apparatus 60 is not limited to these shapes. The dermaplaning apparatus 60 can be used to provide exfoliation of skin within a treatment area, wherein the trimming head 64 with its vibrating blade 66 are moved across a user's skin to gently remove dead skin cells and unwanted hair on the surface of the skin, thereby improving a user's complexion.

Figure 18:
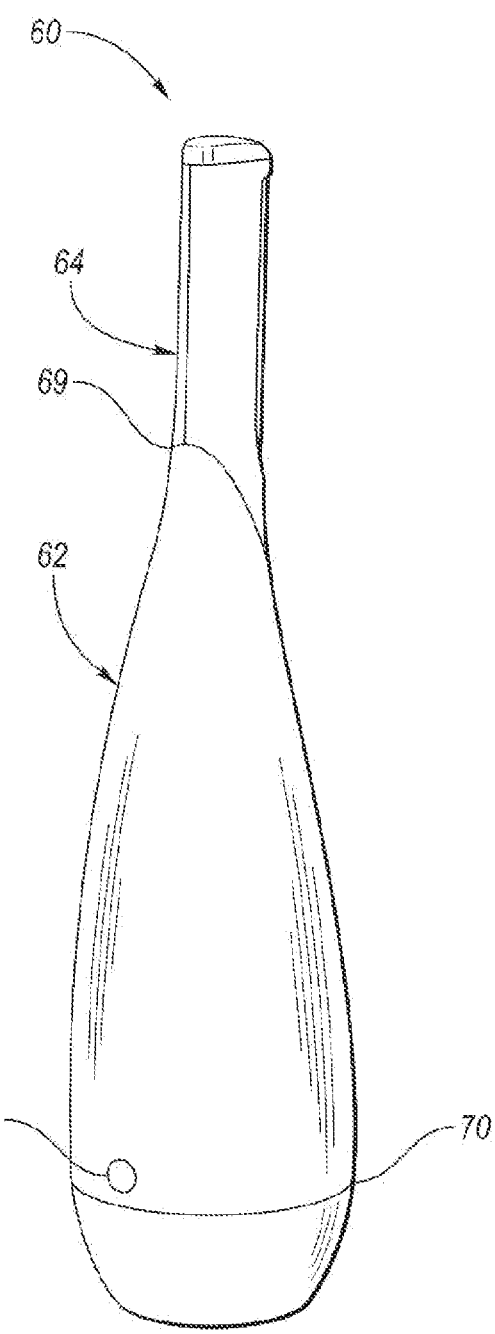
FIG. 18 is a rear perspective view of the dermaplaning apparatus.
Figure 22:
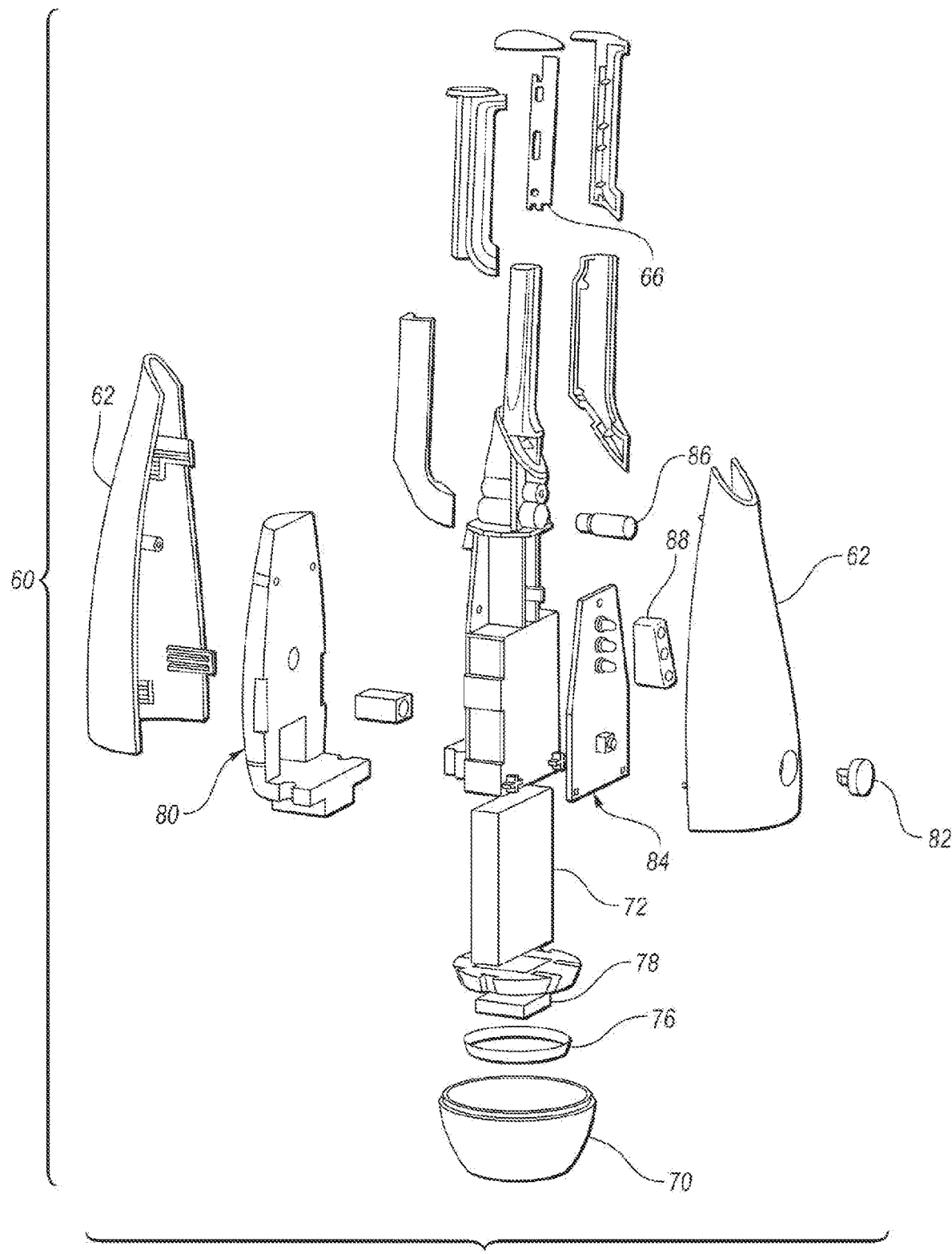
FIG. 22 is an exploded view of the dermaplaning apparatus illustrating internal mechanical and electrical components.

In one or more embodiments, the dermaplaning apparatus 60 is rechargeable and includes an internal rechargeable (e.g. lithium) battery 72 (FIGS. 21 and 22). Induction charging points (not shown) may be provided on the housing 62 and the interior of the charging base 68, and a charging port 74 may be provided on the exterior of the charging base 68. To charge the dermaplaning apparatus 60 via induction charging, the bottom end 70 of the housing 62 may be inserted into the recess of the charging base 68, and the charging base 68 is connected to an electrical outlet or other power source by a charging cord (not shown) received in the charging port 74. Alternatively, the charging port 74 may be provided on the housing 62 for directly charging the dermaplaning apparatus 60, such that the charging base 68 would not be required, as illustrated in FIG. 18.

FIG. 20 is a side perspective view of the bottom end 70 of the housing 62 of the dermaplaning apparatus 60 illustrating a cooling member 76 such as a cooling plate provided on the bottom end 70 of the housing 62. The cooling member 76 may be used to contact and cool skin within a treatment area after exfoliation by the blade assembly 66, or may be generally used for cooling skin at other times or in other regions. In one or more embodiments, the cooling member 76 may be constructed from a metallic material and may be cooled by a thermoelectric cooler or Peltier device or Peltier chip 78 with a heat sink 80, as illustrated in FIGS. 21 and 22 and as described above with respect to the microdermabrasion apparatus 10. In a non-limiting example, the cooling member 76 may be capable of reaching a temperature less than 9 degrees C. in less than 60 seconds and between approximately 0-9 degrees C. in an elapsed time of 60-150 sec. The cooling member 76 can be generally planar and circular- or oval-shaped as shown or could alternatively have other shapes and/or textures.

The dermaplaning apparatus 60 includes a power button 82 which can function to turn the dermaplaning apparatus 60 on and off as well as to toggle through different treatment levels. A motor assembly 86 having an eccentric load is disposed with in the housing 62 (FIGS. 21 and 22) and is operably connected to the blade assembly 66 for generating vibration of the blade 66. A controller or PCB 84 in electrical communication with the motor assembly 86 for providing multiple vibration intensity levels of the blade 66. In one non-limiting example, different speeds of the motor 86 may include a low speed (e.g. 6400 RPM+/−5%) and a high speed (7700 RPM+/−5%) which translate to different blade vibration frequencies. The power button 82 may also be used to power the cooling member 76 on and off.

Indicator lights 88, such as LEDs, may be provided to indicate when the dermaplaning apparatus 60 is powered on and to indicate the selected treatment level. The indicator lights 88 may also be used to indicate charging progress of the battery 72 and the power status of the cooling member 76.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A dermaplaning apparatus, comprising:
   a housing having a top end and a bottom end;
   a trimming head attached to the top end of the housing and having a blade assembly arranged to exfoliate skin within a treatment area;
   a cooling plate provided on the bottom end of the housing and arranged to cool skin within the treatment area;
   a controller disposed within the housing in electrical communication with the trimming head;
   a power button for powering the cooling plate on and off; and
   an indicator on the housing for indicating a power status of the cooling plate.

2. The dermaplaning apparatus of claim 1, wherein the cooling plate is constructed from a metallic material and is cooled via a Peltier device disposed within the housing.

3. The dermaplaning apparatus of claim 1, further comprising a rechargeable battery disposed within the housing.

4. The dermaplaning apparatus of claim 3, further comprising a charging base having a recess arranged to receive the bottom end of the housing, wherein the battery is configured to be inductively charged via power supplied to the charging base.

5. The dermaplaning apparatus of claim 1, further comprising a motor assembly operably connected to the blade assembly for generating vibration of the blade assembly.

6. The dermaplaning apparatus of claim 5, wherein the controller is configured to provide a plurality of vibration intensity levels of the trimming head.

7. The dermaplaning apparatus of claim 1, wherein the trimming head is integral with the housing.

8. The dermaplaning apparatus of claim 1, wherein the trimming head is removably secured to the top end of the housing.

9. The dermaplaning apparatus of claim 1, wherein the blade assembly is removable from the trimming head.

* * * * *